US007697980B1

(12) United States Patent
Laflen et al.

(10) Patent No.: US 7,697,980 B1
(45) Date of Patent: Apr. 13, 2010

(54) TECHNIQUE FOR HIGH SPATIAL RESOLUTION, FOCUSED ELECTRICAL STIMULATION OF ELECTRICALLY-EXCITABLE TISSUE

(75) Inventors: J. Brandon Laflen, Lafayette, IN (US); Thomas M. Talavage, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 916 days.

(21) Appl. No.: 10/419,298

(22) Filed: Mar. 27, 2003

Related U.S. Application Data

(60) Provisional application No. 60/369,759, filed on Apr. 3, 2002.

(51) Int. Cl.
*A61N 1/00* (2006.01)
(52) U.S. Cl. .......................................... 607/2; 607/57
(58) Field of Classification Search ............... 607/2, 607/55–57, 67, 115–116, 154–156
See application file for complete search history.

(56) References Cited

U.S. PATENT DOCUMENTS

| 4,495,384 | A | | 1/1985 | Scott et al. |
| 4,762,135 | A | | 8/1988 | van der Puije et al. |
| 5,123,422 | A | | 6/1992 | Charvin |
| 5,186,181 | A | * | 2/1993 | Franconi et al. ............. 607/156 |
| 5,549,639 | A | * | 8/1996 | Ross .......................... 607/101 |
| 5,792,073 | A | * | 8/1998 | Keefe .......................... 600/559 |
| 6,083,252 | A | * | 7/2000 | King et al. ..................... 607/70 |
| 6,161,046 | A | | 12/2000 | Maniglia et al. |
| 6,491,644 | B1 | * | 12/2002 | Vujanic et al. .............. 600/559 |
| 7,047,074 | B2 | * | 5/2006 | Connelly et al. .............. 607/36 |
| 2002/0038121 | A1 | * | 3/2002 | Rozenberg et al. ............ 606/15 |

OTHER PUBLICATIONS

D.J. Allum, "Basis of Processing Sound Strategies, Introduction to Coding Strategies," [online], undated [retrieved on Sep. 7, 2000]. Retrieved from the Internet: http://www.medel.com/web/us/.
Philipos C. Loizou, "Signal-Processing Techniques for Cochlear Implants," *IEEE Engineering in Medicine and Biology*, May/Jun. 1999, pp. 34-46.

* cited by examiner

*Primary Examiner*—George R Evanisko
(74) *Attorney, Agent, or Firm*—William F. Bahret

(57) ABSTRACT

A tissue stimulation method which uses wave-guiding principles to construct a focused point of stimulation at any location within a region of electrically excitable living tissue. The excitation is formed through the constructive interference of different frequency wave energies, traveling at frequency-dependent velocities, which coalesce at the stimulation point. Further energy is brought to the stimulation point through reflection(s) at the boundaries of the wave-guiding structure. The resulting excitation signal depends upon several factors, including pulse envelope and duration, allowable frequency range, and stimulation time.

8 Claims, 13 Drawing Sheets

TECHNIQUE FOR HIGH SPATIAL RESOLUTION, FOCUSED ELECTRICAL STIMULATION OF ELECTRICALLY-EXCITABLE TISSUE

CROSS-REFERENCE TO RELATED APPLICATION

This application claims the benefit of U.S. Provisional Patent Application Ser. No. 60/369,759, filed Apr. 3, 2002, which application is hereby incorporated by reference along with all references cited therein.

BACKGROUND OF THE INVENTION

This invention relates to methods of stimulating electrically excitable living tissue, e.g., nerves and muscle fibers, and is considered particularly applicable to tissues that demonstrate functional variation with location, such as the tonotopic variation of the spiral ganglia of the auditory nerve, and the spatial variation of motor nerves within the spinal cord.

Within excitable tissue, especially neurons, individual neighboring cells could correspond to functionally unique tasks. In some applications, this results in a high level of resolution within a region of cells. Sensory organs commonly express this type of resolution. For example, the cochlea consists of a helical region of excitable tissue that relates to a mapping of sensed sound frequency from one end to another, and neighboring cells within this region may relate to appreciably different frequencies. Existing technology either creates a specific point of stimulation without the ability to change the location (except for physical adjustment, e.g., electrodes), or has some adjustability but creates a very broad region of stimulation (e.g., magnetic field stimulation). A need exists for technology capable of providing a high degree of stimulation resolution as well as the ability to focus the stimulation at any desired location.

SUMMARY OF THE INVENTION

The invention is a new method of stimulating electrically excitable tissue which employs an implantable waveguide for delivery of an electric field pulse to any desired location along the extent of the tissue. The pulse occurs as a field interference pattern within the cross-sectional geometry of the guide and allows for high spatial resolution in stimulation locations.

The invention has a wide range of applications, including, but not limited to, stimulation of the basilar membrane or spiral ganglia in cochlear implants, stimulation of optic cells in retinal implants, and stimulation of nerve tissue within the spinal column. The primary advantage to this form of stimulation over others is in the ability to focus the stimulation at any desired location, and with a high degree of resolution. However, the method of the present invention is also advantageous because it offers a paradigm of stimulation that is not limited by bundles of wires carrying signals to electrode arrays. Furthermore, the construction of the interference pattern depends solely upon the input signal to the waveguide, which can be easily altered to accommodate future stimulation strategies and paradigms.

DETAILED DESCRIPTION OF PREFERRED EMBODIMENTS

Figure 1:
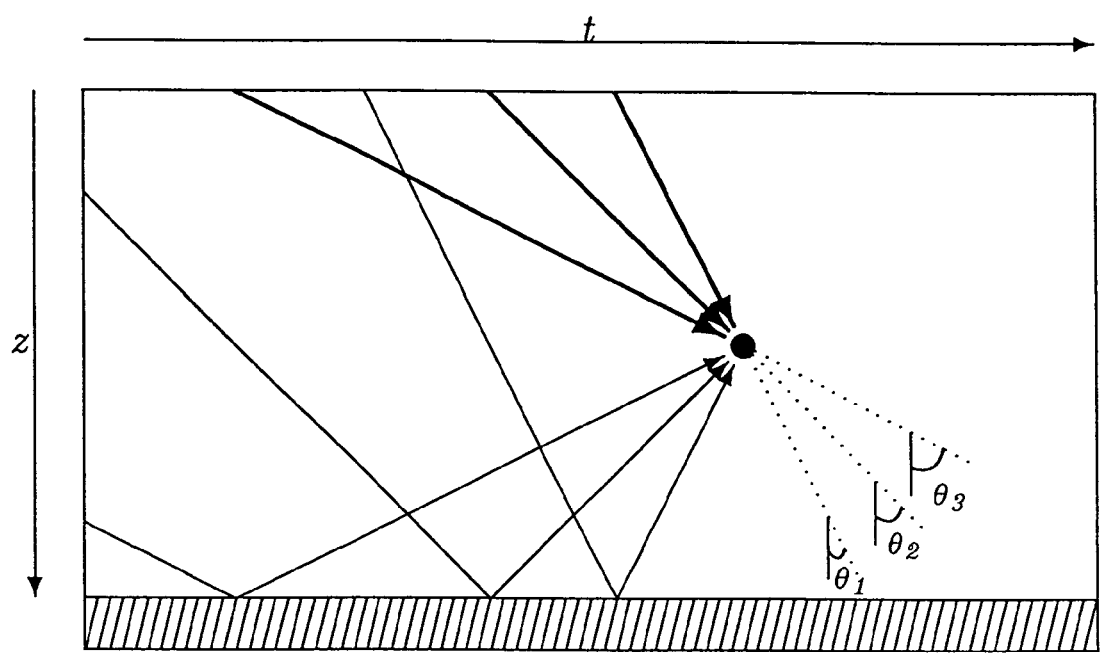
FIG. 1 is a "bounce diagram" of frequency-bands traveling in space and time.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

Geddes and Baker describe in depth the various parameters and considerations for electric field stimulation of electrically-excitable tissue, in *Principles of Applied Biomedical Instrumentation*, 3d ed., John Wiley and Sons, New York, 1989. Various models describe the efficacy of stimulation regimes, but the critical factor in achieving stimulation is the attainment of a critical average current for a given duration of stimulus pulse. The following "strength-duration curve" relates the required average current ($I_{av}$) to the duration (d) and physical parameters of the tissue, rheobase (b) and chronaxie (c):

$$I_{av} = b(1 + c/d) \qquad (1)$$

The electric field pulse for the disclosed technique is constructed to match a single-period, sinusoidal electric-field pulse. The period of the pulse corresponds to the duration (d), and relates to the physical parameter chronaxie, which maximizes the energetic efficiency of the pulse. In humans, chronaxie ranges from 0.01-0.35 ms for nerves and is approximately 3 ms for skeletal muscles. This limits the stimulation frequencies as a practical matter to an order of 10 kHz. Although it is possible to stimulate these tissues with higher-frequency pulses, e.g., up to 100 kHz, the stimulation loses energetic efficiency and runs the risk of causing thermal damage. The actual upper limit for "safe" stimulation frequencies will depend upon the application.

The amplitude of the electric-field pulse also depends upon each application. The average field in each pulse will lead to an average current density, depending upon the conductivity of the tissue. This average current density leads to the average current ($I_{av}$), depending upon the geometry of the field cross-section upon the tissue. Lumped together, these factors contribute to the rheobase, and in general must be experimentally determined. Strength and duration requirements are investigated for the individual application and the field strength and pulse frequency range are selected to reflect these parameters.

As indicated above, the invention creates a high spatial resolution region of electric-field excitation within any location along the extent of a given electrically-excitable tissue. The excitation is delivered by a waveguide, and as such its cross-sectional field must interact with the tissue, with the electric-field perpendicular to the tissue. Additionally, the guide itself must conform to any requirements created by the cavity or tissue geometry.

One well known property of wave energies traveling within wave-guiding structures is the propagation constant $$\beta \propto \sqrt{1 - \left(\frac{f}{f_c}\right)^2}, \quad (2)$$

where $f_c$ is the cutoff frequency and intrinsic to the geometry and material properties of the wave-guiding structure. See, for example S. Ramo, J. R. Whinnery, and T. Van Duzer, Fields and Waves in Communication Electronics, 3d ed., John Wiley and Sons, Inc., New York, 1994 (hereby incorporated by reference). This property leads to a frequency-dependent velocity, associated with the center frequency, $f_i$, of a given frequency-band, known as the group velocity:

$$v_i \doteq \frac{\partial}{\partial \beta} 2\pi f = v_M \sqrt{1 - \left(\frac{f_c}{f_i}\right)^2}, \quad (3)$$

where $v_M$ is the theoretical maximum velocity within the structure. Frequency-bands of wave energies, centered at different frequencies above cutoff, travel along the wave-guiding structure at differing group velocities dictated by (3).

Taking advantage of this property, we construct a waveform composed of many frequency-bands, each centered at a different center-frequency. Further, each frequency-band is appropriately delayed such that all bands coalesce at a predetermined point in space along the wave-guiding structure (the target), to produce maximal constructive interference. FIG. 1 illustrates the concept of multiple frequency-bands coalescing to produce such a peak. In the diagram, space is vertical, increasing from top to bottom. Time is horizontal, increasing from left to right. Vectors represent the location of the center of a given frequency-band pulse in both time and space. Frequency-bands (thick lines) traveling from the entrance of the wave-guiding structure coalesce at a target (circle). The velocities of each band are related to the approach vector angles, $\theta_{\{1,2,3\}}$. Additional frequency-bands (thin lines), returning from the reflecting boundary (cross-hatch) at the end of the structure, bring a second group of coalescing energy to the target.

In order to minimize the extent of overlap among N pulses when not at the target, the center-frequencies (and corresponding velocities) are adjusted such that the angles of the approach vectors for the frequency bands are linearly spaced between the minimum and maximum allowable angles. As shown in FIG. 1, the velocity of each frequency-band is related to the angle of its approach vector in time-space: $\theta_i = \cot^{-1} v_i \leftrightarrow v_i = \cot \theta_i$. The minimum and maximum allowable angles correspond to group velocities $v_H$ and $v_L$, respectively. A linear spacing across the angles is used to designate N group velocities between $v_L$ and $v_H$ ($1 \leq i \leq N$):

$$v_i = \cot\left(\cot^{-1} v_L + \frac{i-1}{N-1}(\cot^{-1} v_H - \cot^{-1} v_L)\right). \quad (4)$$

Using (4), we construct a continuous frequency distribution by replacing the $(i-1)/(N-1)$ term with a continuous percentile: $p \in [0, 1]$. Solving for p yields $$p = \frac{\cot^{-1} v_p - \cot^{-1} v_L}{\cot^{-1} v_H - \cot^{-1} v_L}. \quad (5)$$

Taking the derivative with respect to the continuous group velocity, $v_p$, produces a density function for all group velocities $v_p \in [v_L, v_H]$. Group velocities are related to center frequencies by (3); substituting (3) into this density function yields a scaling function for all center frequencies $f_p \in [f_L, f_H]$:

$$dp(f_p) = -\left(1 + v_M^2\left(1 - \left(\frac{f_c}{f_p}\right)^2\right)\right)^{-1} (\cot^{-1} v_H - \cot^{-1} v_L)^{-1}, \quad (6)$$

$$v_{\{L,H\}} = v_M \sqrt{1 - \left(\frac{f_c}{f_{\{L,H\}}}\right)^2}. \quad (7)$$

dp is used to scale the continuous contribution of frequency-bands centered at center-frequencies within the given range. All contributions combine to produce a single stimulation waveform.

The stimulation waveform at the target is composed of frequency bands centered on a continuous distribution of center frequencies. The center frequency scaling function, dp, defined in (6), appropriately scales the contributions of these frequency bands so that overlap, and therefore constructive interference, is minimized away from the target.

Consider a given frequency-band as the spectrum of a corresponding short-duration pulse envelope in time, such that $$S(t_p, 2\pi f) = \int_{-\infty}^{+\infty} env(t_p, t) e^{-j2\pi ft} \partial t \quad (8)$$

is the spectrum, where $t_p$ is the duration of the pulse in time and $env(t_p, t)$ is the pulse envelope. As will be shown, variable pulse duration can lead to variable minimum and maximum allowed center frequencies, such that $f_p \in [f_L(t_p), f_H(t_p)]$. This leads to a dependence of dp on both center frequency and pulse duration: $dp(t_p, f_p)$. Using this modified dp with the pulse envelope spectrum S, we construct a stimulation waveform at the target:

$$F(2\pi f) = \int_{\tau = t_p^{MIN}}^{t_p^{MAX}} A(\tau) \int_{\xi = f_L(\tau)}^{f_H(\tau)} B(\xi) dp(\tau, \xi) S(\tau, 2\pi(f - \xi)) \partial \xi \partial \tau. \quad (9)$$

$A(t_p)$ and $B(f_p)$ are selection functions for isolating certain elements of pulse duration or center frequency, respectively; in general, they are specific values such as unity or a delta function at a desired quantity.

In (9), $f_L$ and $f_H$ (and therefore also dp) are functions of pulse duration. The bandwidth, $f_w$, of spectrum S (equation 8) is intrinsically related by a specific proportionality constant, $\alpha$, to the pulse duration of the envelope[1]

[1] Generally, if the pulse duration is finite, the total width of the spectrum (i.e., the total extent of non-zero elements) is infinite. However, the envelopes considered here exhibit corresponding spectra with effectively finite bandwidths, due to the roll-off of the spectral energy.

$$f_\omega = \frac{\alpha}{t_p}. \tag{10}$$

The minimum and maximum allowable center frequencies depend upon the required bandwith and are therefore dependent upon the pulse duration. Generally for a given bandwidth $$f_L = f_B + \frac{f_w}{2}, \tag{11}$$

$$f_H = f_{MAX} - \frac{f_w}{2}, \tag{12}$$

where $f_B$ is the base frequency associated with the base or smallest allowed velocity, and $f_{MAX}$ is the maximum allowed frequency within the application. [2] dp is similarly dependent upon $t_p$ since it is a function of $f_L$ and $f_H$ (equation 6).

[2] For a given application, frequencies below $f_B$ will propagate too slowly or will be attenuated (below cut-off), while frequencies above $f_{MAX}$ are too high for reasonable stimulation. Therefore, the actual excitation signal should be band-limited.

The waveguide excitation signal is derived from $F(2\pi f)$, which completely describes the stimulation waveform, coalesced at the target location. This derivation is accomplished by phase shifting the spectrum back to the entrance of the waveguide:

$$F(2\pi f)e^{j\beta'(f)z_t} \tag{13}$$

where $z_t$ is the location of the stimulation target along the structure and $$\beta'(f) = \begin{cases} \beta(f) & \text{if } f_B \leq f \leq f_{MAX} \\ 0 & \text{otherwise} \end{cases} \tag{14}$$

This compensates for the group dispersion (within the allowed frequency range) while also introducing a negative delay in time (i.e., the signal is moved backwards in time). To ensure that the excitation signal occurs after time zero, an additional phase term is introduced to counteract the time delay and to shift the entire pulse into the range $t > 0$ $$F(2\pi f)e^{j\beta'(f)z_t}e^{-2\pi f(t_t+t_p/2)}. \tag{15}$$

Here, $t_t = z_t/v_B$ is the amount of time it will take the base frequency energy to travel to the target ($z_t$).

A second stimulation waveform can be brought to the target by placing a reflecting boundary at the far end of the wave-guiding structure (see FIG. 1). This waveform is identical to the first except negative before reflection. Because the second waveform arrives at the target after reflection, additional delay is added to the first waveform such that both arrive at the same time. Thus, with a second waveform $$z_{t1} = z_t, \tag{16}$$

$$z_{t2} = 2L - z_t, \tag{17}$$

$$t_{t1} = t_{t2} = \frac{z_{t2}}{v_B}, \tag{18}$$

where L is the length of the waveguiding structure, and the final compensation is:

$$F(2\pi f)[e^{j(\beta'(f)z_{t1} - 2\pi f(t_{t1}+t_p/2))} - e^{j(\beta'(f)z_{t2} - 2\pi f(t_{t2}+t_p/2))}] \tag{19}$$

(the second term is subtracted from the first to account for the reflection). The excitation signal delivered to the waveguide is therefore $$e(t) = \frac{1}{2\pi} \int_{-\infty}^{+\infty} F(2\pi f) [ \tag{20}$$

$$e^{j(\beta'(f)z_{t1} - 2\pi f(t_{t1}+t_p/2))} - e^{j(\beta'(f)z_{t2} - 2\pi f(t_{t2}+t_p/2))}] e^{j2\pi ft} \partial f.$$

It is important to design the wave-guiding structure to maximize the velocity spread within the given frequency range, thus decreasing the amount of constructive interference away from the target. Since the geometry of the structure is dictated largely by the stimulation paradigm, the main design parameter is the cutoff frequency, $f_c$. The cutoff should be chosen to maximize the velocity spread:

$$f_c^* = \arg \max_{f_c \in (0, f_{MAX})} (v_H - v_L) \tag{21}$$

There is a strong interdependence on $f_c$ in (21). Both $v_L$ and $v_H$ are related to $f_c$ and also to $f_L$ and $f_H$, respectively, through the group velocity equation (equation 7). $v_M$ (a term in the group velocity equation) is also related to $f_c$:

$$v_M = \frac{2\pi f_c}{A}, \tag{22}$$

where A is a lumped parameter representing the dimensions and geometry of the wave-guiding structure. $f_L$ and $f_H$ can be rewritten in terms of (11) and (12), emphasizing a dependence on pulse duration, $t_p$ (through bandwidth, $f_w$; equation 10), as well as $f_c$.

Proceeding from (11) and (12), two independent variables, $f_{MAX}$ and $f_B$ must be determined. $f_{MAX}$, is given by the application; $f_B$ can be expressed in terms of $v_B$ (base velocity, the lowest allowed velocity for the application), by solving the group velocity equation (equation 3) for $f_B$ and combining with (22):

$$f_B = \frac{f_c}{\sqrt{1 - \left(\frac{v_B A}{2\pi f_c}\right)^2}}. \tag{23}$$

Combining (7), (11), (12), (21), and (23) yields an expression for the cutoff based on optimal velocity spread:

$$f_c^* = \arg\max_{f_c \in (0, f_{MAX})} \left\{ \frac{2\pi f_c}{A} \left[ \sqrt{1 - \left(\frac{f_c}{f_{MAX} - \frac{f_w}{2}}\right)^2} - \sqrt{1 - \left(\frac{f_c}{\sqrt{1-(v_B A/(2\pi f_c))^2} + \frac{f_w}{2}}\right)^2} \right] \right\}. \quad (24)$$

This expression depends upon $f_{MAX}$, A, and the two timing-related parameters, $f_w$ and $v_B$.

Both timing-related parameters $f_w$ and $v_B$ are controlled by the free variable, $t_p$, the pulse duration. Bandwidth is directly related to the pulse duration by (10). Base velocity figures into the overall stimulation time:

$$t_{STIM} = t_p + \frac{4L}{v_B}, \quad (25)$$

$$v_B = \frac{4L}{t_{STIM} - t_p}, \quad (26)$$

where L is the length of the waveguide and $4L/v_B$ represents the longest possible stimulation time: forward and reflected stimulation waveforms both traveling to the reflecting end of the structure and returning, with a target at the entrance. When $t_p$ is not specified directly by the application, (10) and (26) can be substituted into (24) to yield an expression simultaneously dependent upon $f_c$ and $t_p$.

Figure 2:
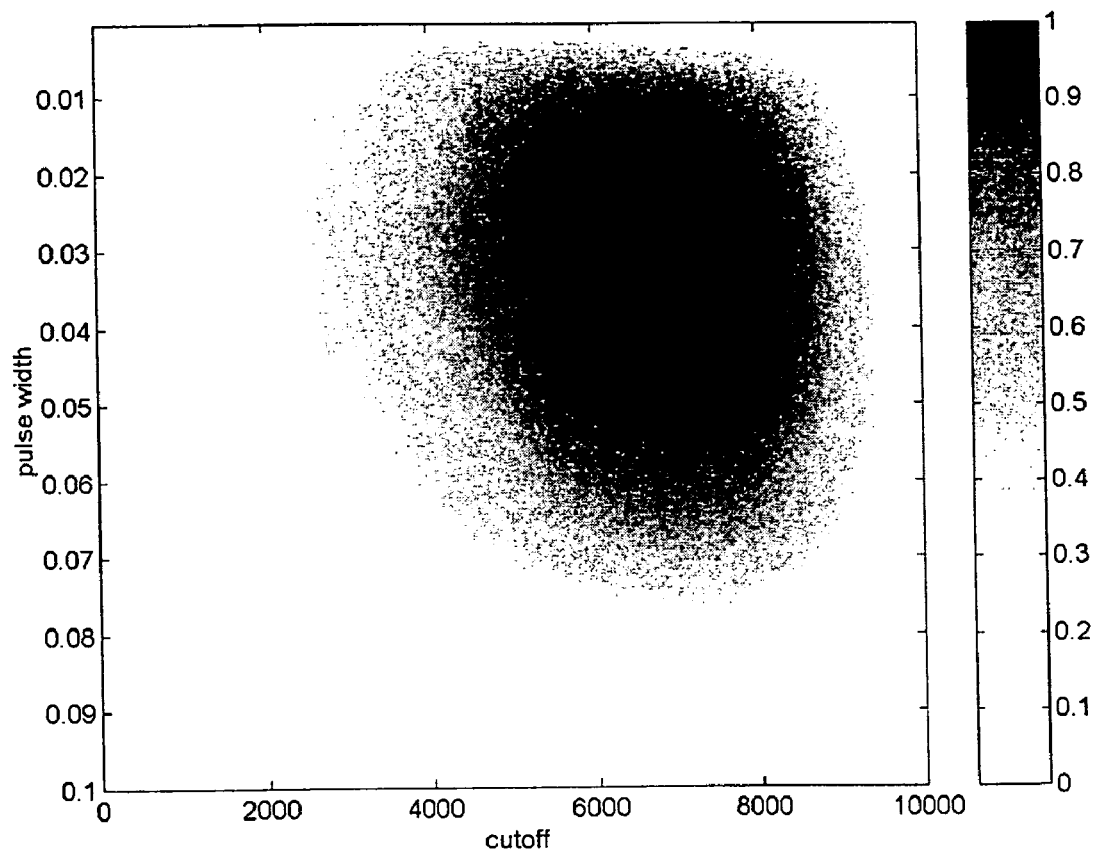
FIG. 2 is a plot of velocity spread as a function of cutoff frequency, $f_c$, and pulse width or duration, $t_p$.

FIG. 2 illustrates the typical dependence of the velocity spread upon $f_c$ and $t_p$. This plot is normalized so that the maximum velocity spread is unity. Illegal regions (e.g., those regions in which the sum of cutoff and bandwidth exceeds maximum frequency) are given a score of zero. Shorter pulse durations are generally non-optimal because the increased bandwidth reduces effective frequency range. Longer pulse durations are also non-optimal because $v_B$ (equation 26) grows, approaching the maximum velocity. In general, $f_c$ and $t_p$ can be simultaneously determined (to a given degree of accuracy) by a variety of computational algorithms.

Figure 3A:
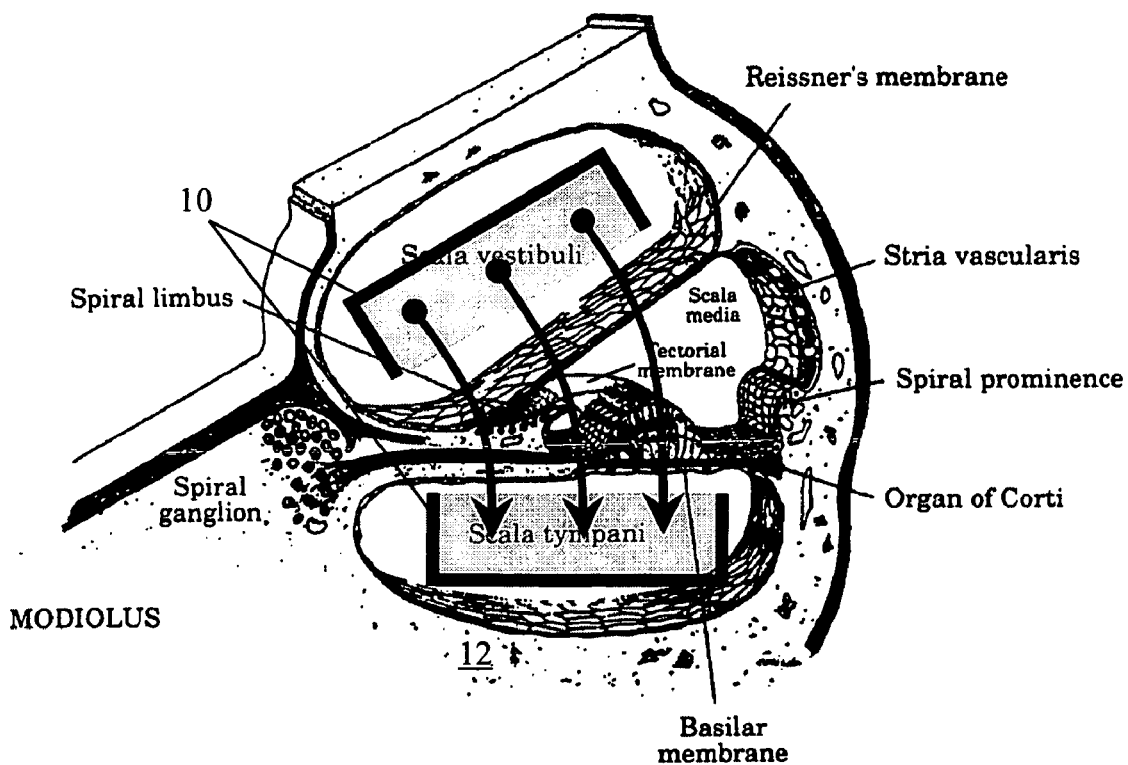
FIGS. 3A and 3B are cross-sectional illustrations of two embodiments of waveguides within the cochlea.

This invention has a variety of applications from implantable devices (e.g., cochlear implants) to external stimulation (e.g., external defibrillation). A first embodiment of a device according to the present invention is a small-scale implantable rectangular electromagnetic waveguide suitable to the dimensions of the cochlea, as shown in FIG. 3A. A second embodiment is a large-scale external parallel plate waveguide. Referring to FIG. 3A, the spiral ganglia of the auditory nerve send receptive projections into the basilar membrane, a thin wall dividing two canals within the cochlea. Each canal is accessed through a window at the base of the cochlea. Each spiral ganglion cell is considered to be responsible for a different frequency sensitivity within the range of human hearing, with frequency descending from the base to the apex of the cochlea. In the case of severe hearing loss, the sound spectrum is often resolved into prominent characteristic frequencies (formants) which are used to identify stimulation locations (individual spiral ganglion cells) within the cochlea.

Figure 3B:
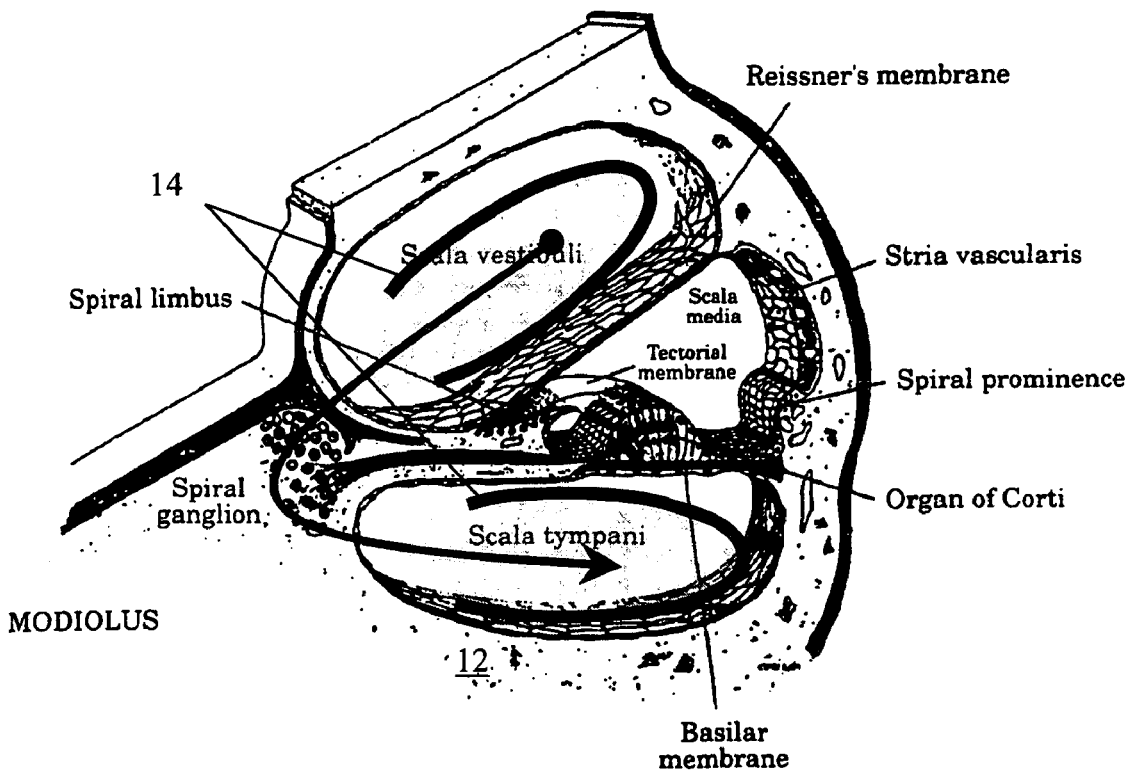

In designing the waveguide device for stimulating the cochlea in accordance with the present invention, the first consideration must be made for access to the spiral ganglia. Typical implants gain access through the oval window into the scala vestibuli; a waveguide using a similar route needs to be flexible to accommodate the twisting cavities of the canals. The second consideration must be made for actual stimulation. FIG. 3A shows a field configuration for a guide set to stimulate the projections of the spiral ganglia within the basilar membrane. As an alternative for cases in which the basilar membrane has been damaged, FIG. 3B shows a field configuration for a guide set to stimulate the spiral ganglia directly. The waveguide of FIG. 3A is shown as having two flexible halves each having a cross-section of approximately 1 mm by 2 mm, each half of the guide having an open rectangular, generally U-shaped structure—open toward the other half—filled with a suitable dielectric material. The traveling wave energies between the two halves cross the basilar membrane which houses the dendritic projections of the auditory nerve. FIG. 3B shows a guide 14 having two separate rod-shaped waveguides, which may be elliptical in cross-section, one having relative positive polarity and the other having relative negative polarity, designed to produce tissue stimulation primarily with the fringe effect of the waveguides. In each case the guide preferably has a length of approximately 30 mm.

The dimensions and geometry of the waveguides dictate the lumped physical parameter, A, in (22). As described in Ramo et al., supra, rectangular waveguides are governed by the cutoff equation $$2\pi f_{c_{m,n}} = v_M \left[ \left(\frac{m\pi}{a}\right)^2 + \left(\frac{n\pi}{b}\right)^2 \right]^{\frac{1}{2}}. \quad (27)$$

For this application, we use the mode $\{m,n\}$ $\{1, 1\}$ with a square cross-section (i.e., a=b); substituting (22) yields an expression for the lumped physical parameter $$A = \frac{\pi\sqrt{2}}{a}, \quad (28)$$

where a is the cross-sectional width and height of the waveguide. The cutoff equation for parallel plate waveguides is $$2\pi f_{c_m} = \frac{m\pi v_M}{a}, \quad (29)$$

leading to lumped parameter $$A = \frac{\pi}{a}, \quad (30)$$

where a is the separation between the plates (with m=1). Simulations of the small-scale, implantable waveguide were performed with parameters a=1 mm and L=30 mm. FIG. 3A illustrates the anatomic placement of this waveguide. For simulations of the large-scale, external waveguide, we chose parameters a=1/√32 m (analogous to a=¼ m within the rectangular guide) and L=2.5 m.

Simulations of the traveling waveforms were conducted using discrete fast Fourier trans-form (FFT) and inverse fast Fourier transform (IFFT) techniques on a PC. The sampling frequency, $f_s$, was always at least three times the Nyquist frequency (i.e., six times the highest frequency, $f_{MAX}$).[3] Motivated by the propagation constant for rectangular waveguides, the spatial sampling was chosen as $k_{z_s} = (2\pi/v_M)\sqrt{f_s^2 - f_c^2}$. The excitation waveform was calculated using a trapezoidal summation approximation to (9) and then computing (20). Similarly, field-intensity as a function of time was computed at each of the $k_{z_s}L$ sample points by applying the phase term $e^{-j\beta(f)z}$ to the spectrum of the excitation waveform and accounting for reflections.

[3] In order to accommodate the dFFT algorithm, the number of actual samples was a power of 2 (i.e., $2^n$). The smallest such power was chosen such that $f_s = 2^n/t_{STIM} \geq 6 f_{MAX}$.

A half-cosine function was used as the pulse envelope for all simulations:

$$env(t_p, t) = \begin{cases} \cos\left(\pi \frac{t}{t_p}\right) & \text{if } |t| < \frac{t_p}{2} \\ 0 & \text{otherwise} \end{cases} \quad (31)$$

The effective bandwidth of the spectrum for this envelope was measured as the symmetric width of two zero-crossings, leading to $\alpha=5$ for (10). The scaling functions (equation 9) were set to $$A(t_p) = \delta(t_p - t_{pBEST}) \quad (32)$$

$$B(f_p) = 1 \quad (33)$$

where $T_{pBEST}$ is the optimal value for $t_p$ from the solution of (21).

Figure 4:
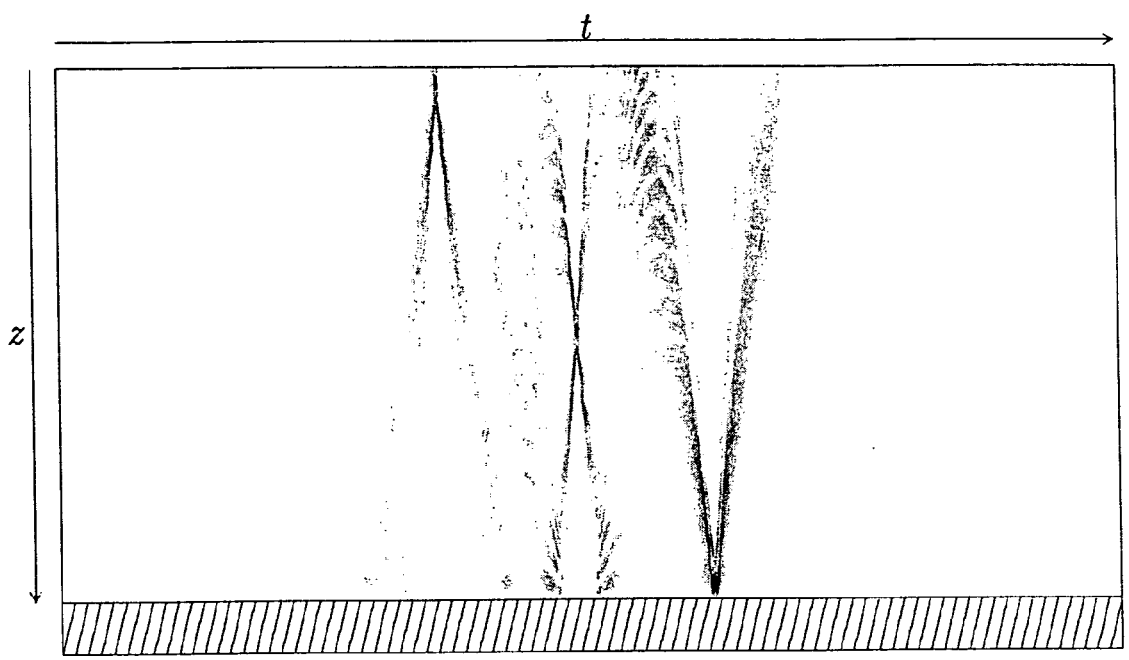
FIG. 4 is a plot of the absolute value of the field intensity as a function of time and position within the small-scale, cochlear waveguide of FIG. 3A.

Using the above simulator, the small- and large-scale embodiments were tested with a variety of parameters: $f_{MAX} = \{10, 100\}$ kHz; $t_{STIM} = \{0.01, 0.05, 0.1, 0.5, 1.0\}$ s; overlap=$\{50, 60, 70, 80, 90, 95, 99\}$%; and $z_t = \{1, 5, 10, 15, 20, 25, 29\}L/30$. FIG. 4 demonstrates typical results for the simulations. In the drawing, the axes are oriented the same as those in FIG. 1, with distance vertically from 0 mm (top) to 30 mm (bottom), and time horizontally from 0 s (left) to 0.14 s (right). Three separate stimulation waveforms have been excited over the simulation time with 80% overlap, $t_{STIM}=0.1$ S, $f_{MAX}=10$ kHz, and $z_t=\{1, 15, 29\}$ mm. The resulting constructive interference and, hence, focused stimulation is apparent in the middle of the waveguide (15 mm) and at 1 mm from each end.

Figure 5:
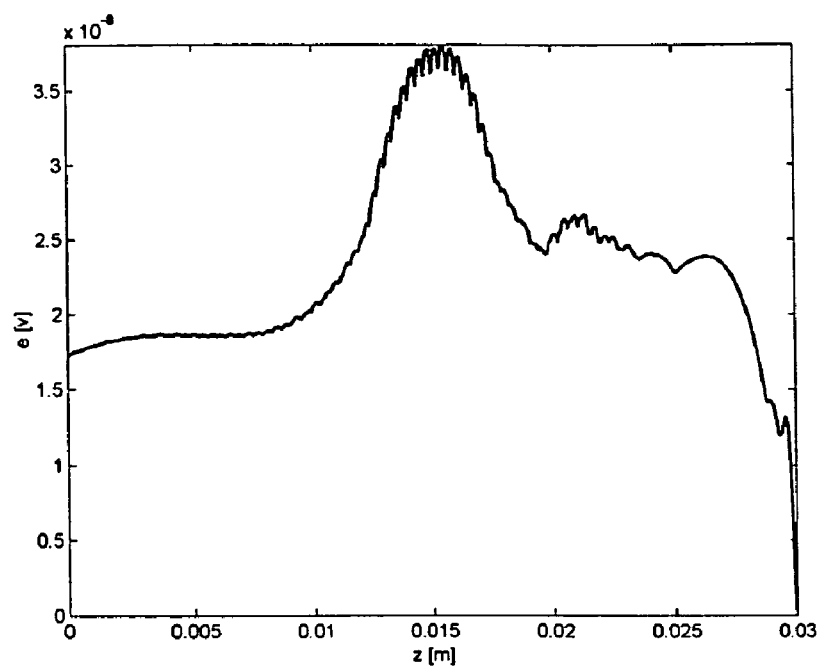
FIGS. 5A and 5B are plots of field intensity as a function of location in the waveguide of FIG. 3A, for comparison of spatial resolution without and with a reflecting boundary, respectively.
Figure 5:
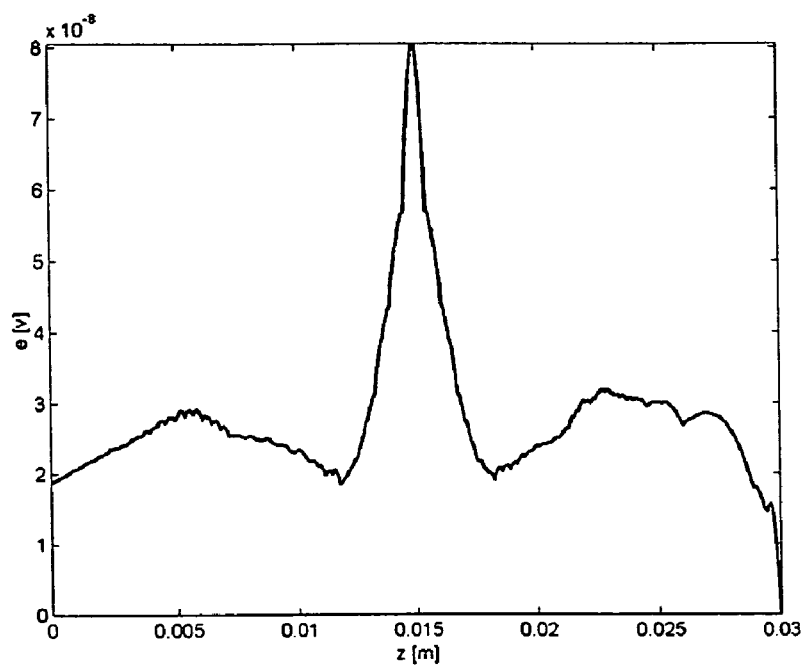

FIGS. 5A and 5B illustrate the effect of utilizing a reflecting boundary at the far end of the wave-guiding structure. These spatial resolution plots show the maximum absolute field intensity across the simulation time for each spatial sample point. FIG. 5A is a plot of data obtained without a reflecting boundary, while FIG. 5B shows the corresponding data for the waveguide with a reflecting boundary. $f_{MAX}=100$ kHz, $t_{STIM}=0.1$ s, and $z_t=15$ mm for both plots. As can be seen in FIG. 5, the additional reflected energy brought to the target increases the spatial resolution. For this reason, the reflecting boundary condition was used for all other simulations described herein.

Figure 6:
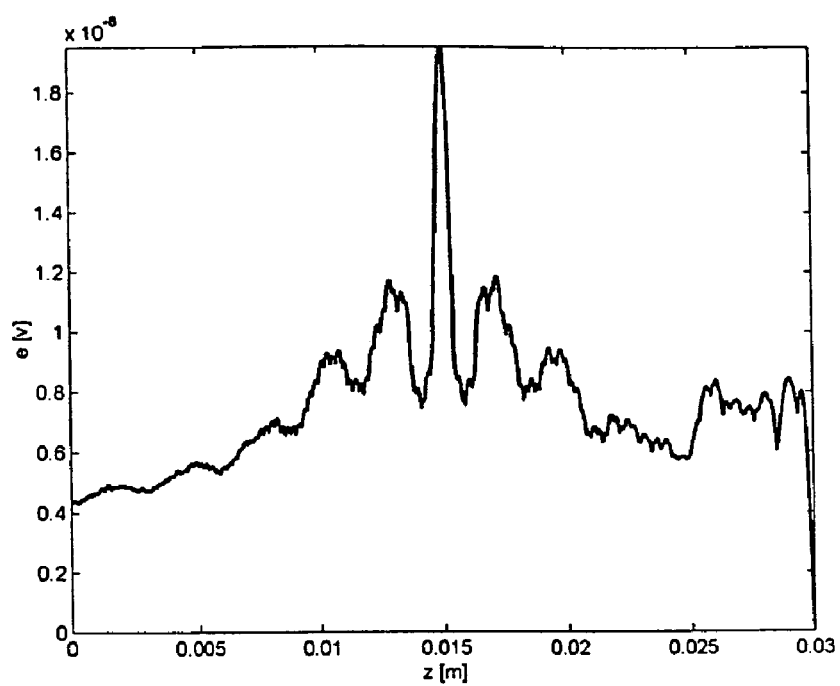
FIGS. 6A through 6D illustrate the effect on spatial resolution of varying $t_{STIM}$.
Figure 6:
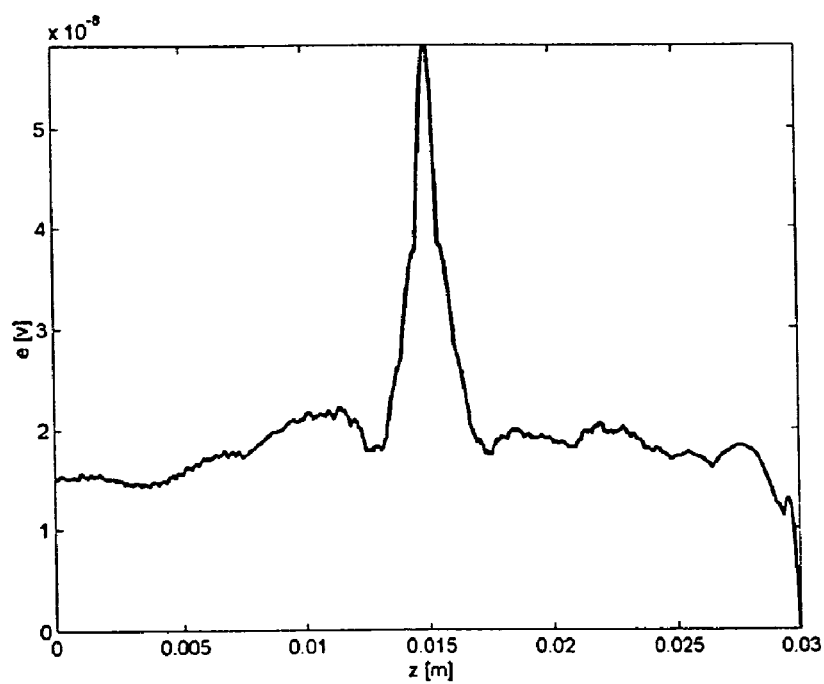
Figure 6:
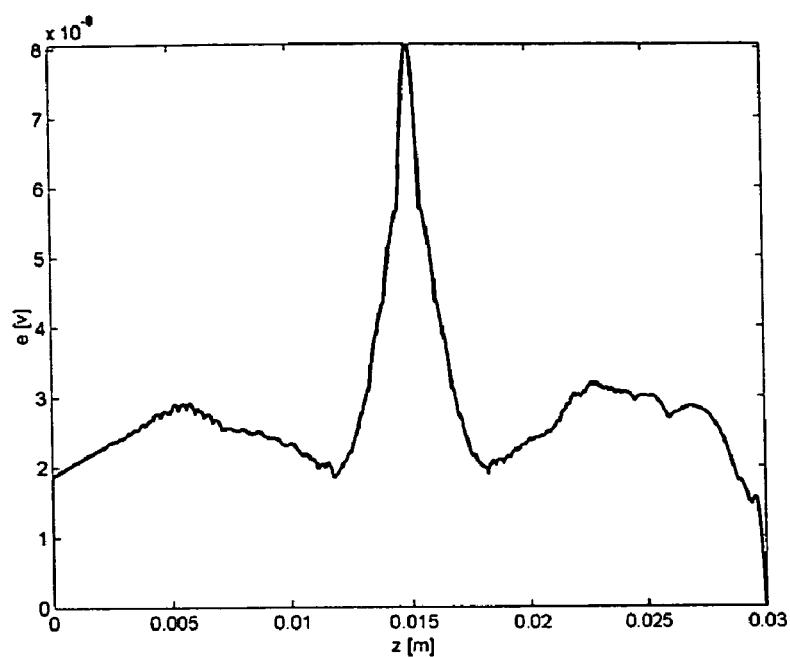
Figure 6:
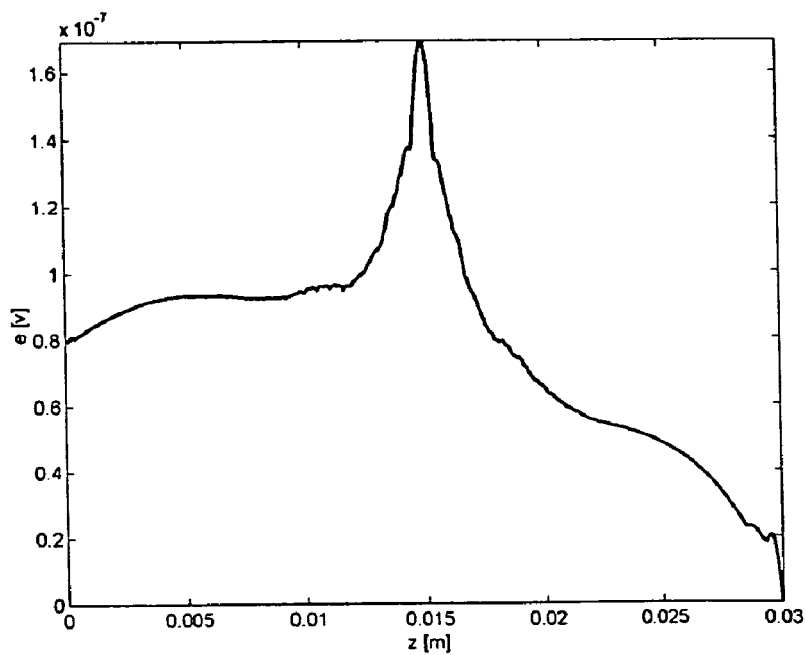
Figure 7:
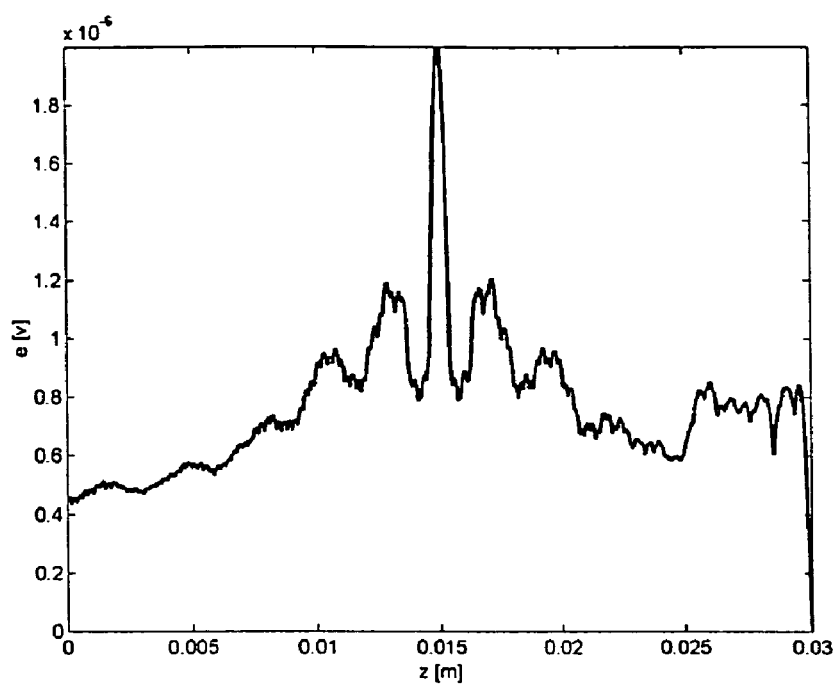
FIGS. 7A and 7B illustrate the effect on spatial resolution of varying $f_{MAX}$.
Figure 7:
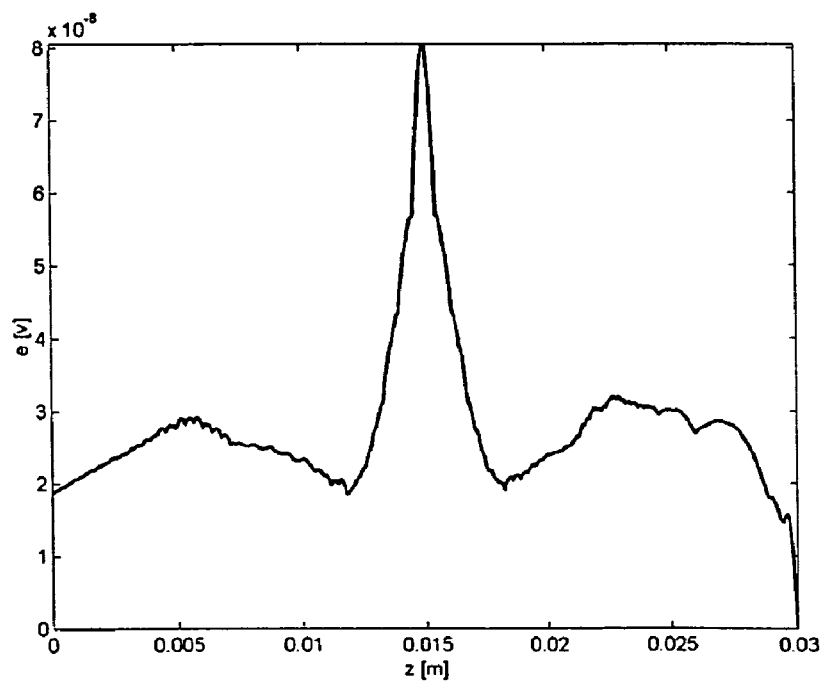
Figure 8:
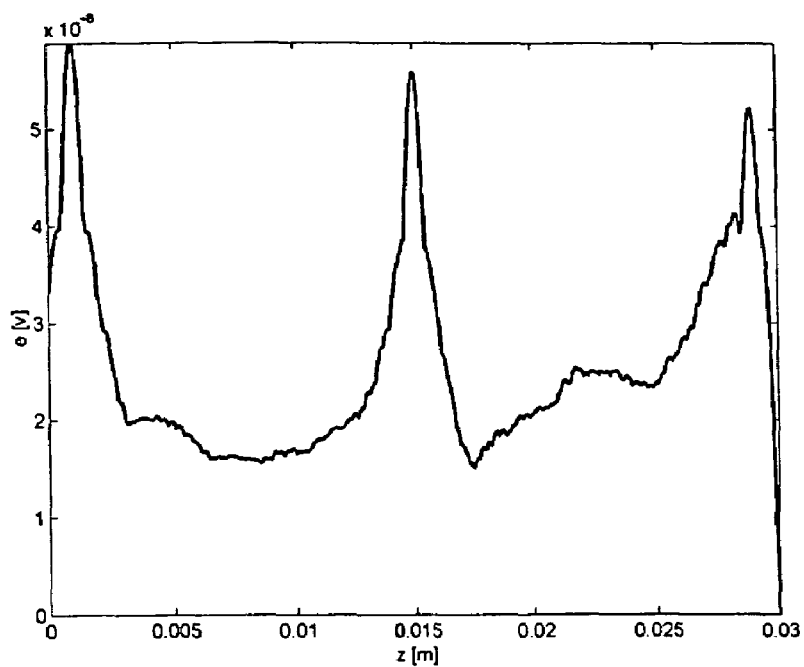
FIGS. 8A through 8D illustrate the effect on spatial resolution of varying percent overlap among successive waveforms.
Figure 8:
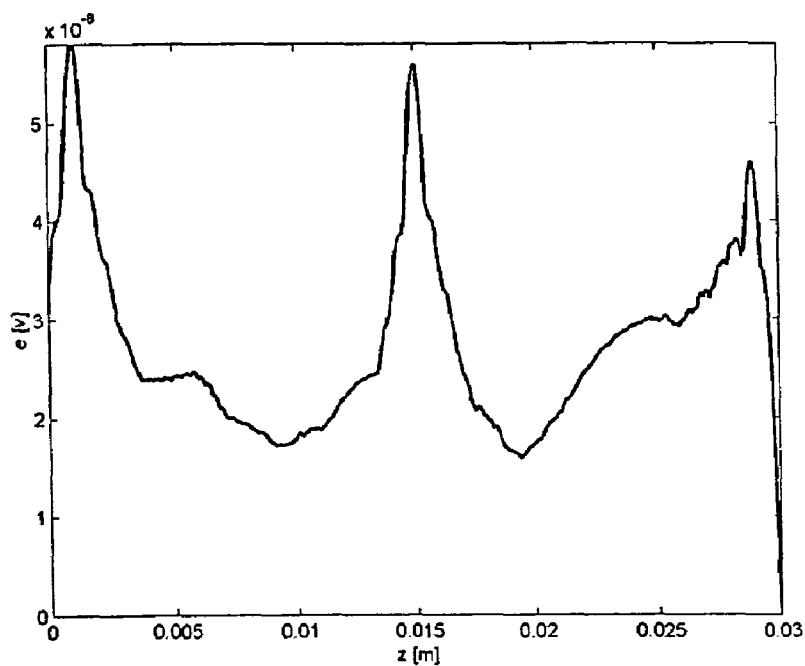
Figure 8:
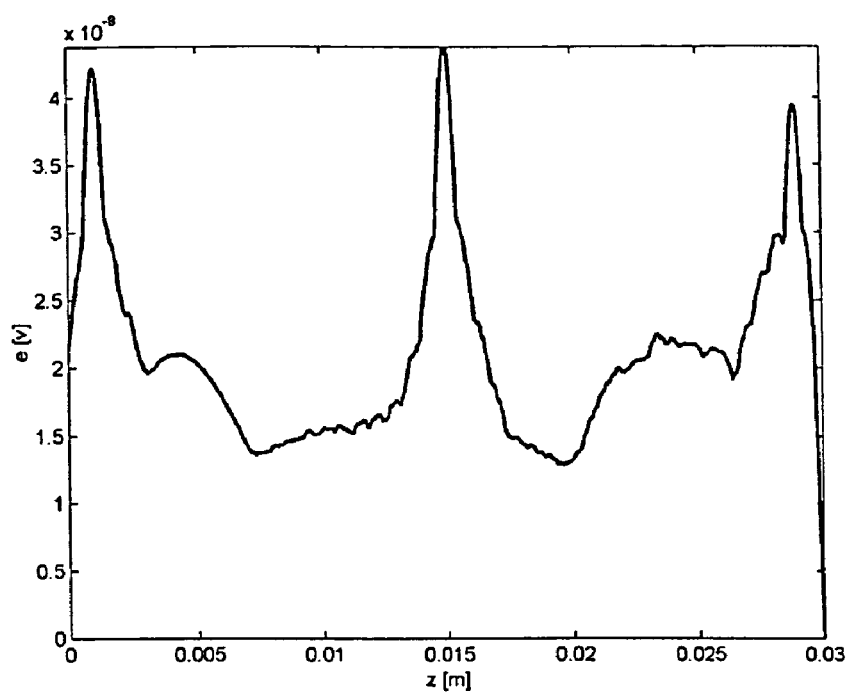
Figure 8:
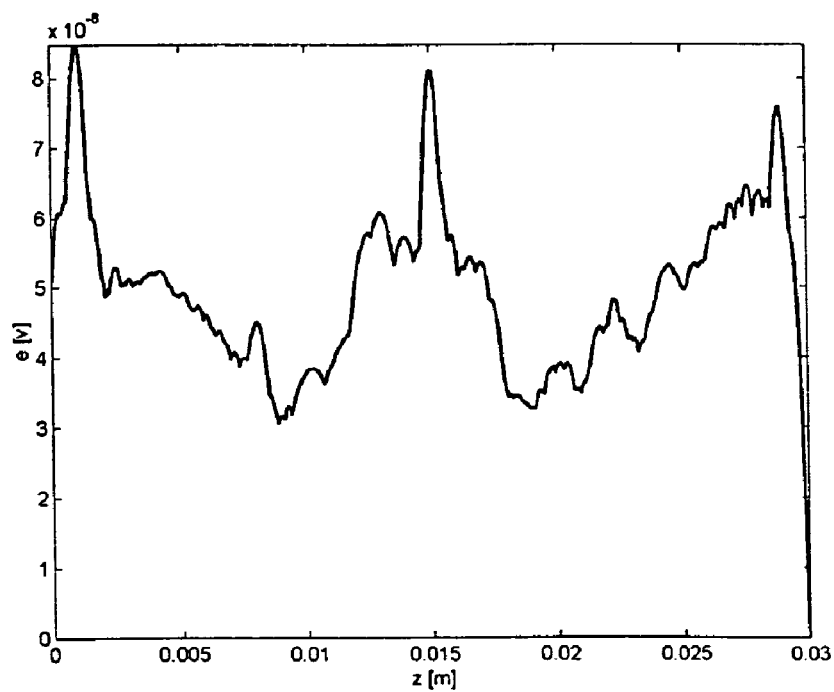

FIGS. 6, 7, and 8 illustrate the results of varying $f_{MAX}$, $t_{STIM}$, and percent overlap among successive waveforms, respectively, in the small-scale, cochlear waveguide. These spatial resolution plots show the maximum absolute field intensity across the simulation time for each spatial sample point. In FIG. 6, $t_{STIM}$ varies from FIGS. 6A to 6D as 0.01, 0.05, 0.1, and 0.5 s. $f_{MAX}=100$ kHz and $z_t=15$ mm for all plots. For FIGS. 7A and 7B, $f_{MAX}=10$ and 100 kHz respectively. $t_{STIM}=0.1$ s and $z_t=15$ mm for both plots. Percent overlap varies from FIG. 8A to FIG. 8D as 80%, 90%, 95%, and 99%. $f_{MAX}=100$ kHz, $t_{STIM}=0.1$ S, and $z_t=1, 15, 29$ mm for all plots.

Tables 1, 2, and 3 summarize the relative gain, 50% spatial gain resolution, and 75% spatial gain resolution (respectively) for parameter combinations with $z_t=L/2$. Relative gain was calculated as the maximum signal at $z=z_t$ divided by the maximum signal at the input (z=0). Spatial gain resolution was calculated as the percentage of signal spatially above 50% (75%) signal gain across the waveguide length.

Figure 9:
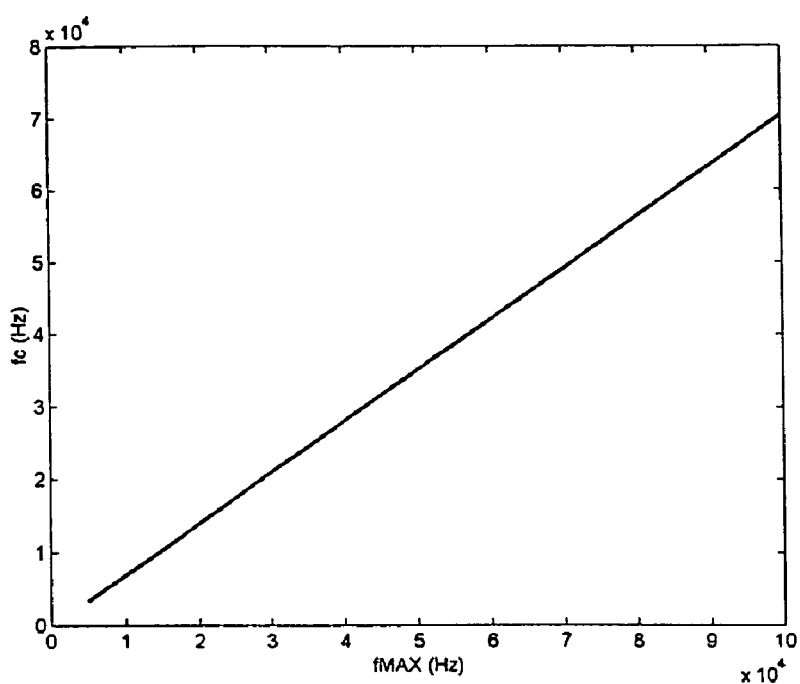
FIGS. 9A and 9B illustrate typical optimal values for $f_c$ and $t_{pBEST}$, respectively, as functions of $f_{MAX}$ (according to eqtn. 21).
Figure 9:
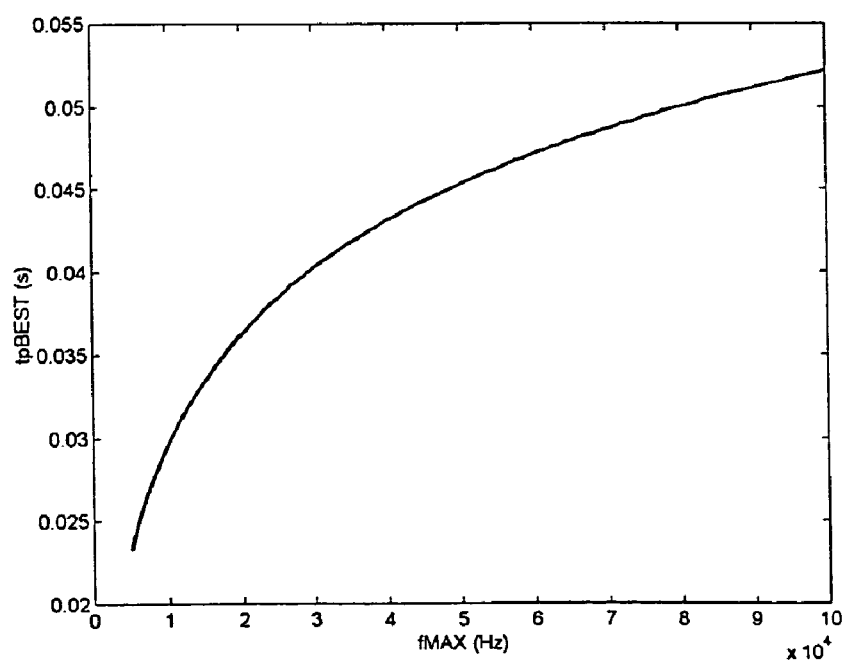

FIG. 9A illustrates the effects of varying $f_{MAX}$ upon the optimal values of $f_c$ while FIG. 9B illustrates the effects of varying $f_{MAX}$ upon the optimal values of $t_{pBEST}$.

Generally, there is an increase in relative peak height and a broadening of spatial peak width associated with increases in either $f_{MAX}$ or $t_{STIM}$. However, percent overlaps $\leq 95\%$ appear to have a minimal impact on spatial resolution. The gain and spatial resolution values

TABLE 1

| $t_{STIM}$ | $f_{MAX}$ = 10 kHz | $f_{MAX}$ = 100 kHz |
|---|---|---|
| | full-body, $|A \cdot L| = 10\pi\sqrt{2}$ | |
| 0.01 s | 1.995 | 2.954 |
| 0.05 s | 2.405 | 3.538 |
| 0.10 s | 2.954 | 3.128 |
| 0.50 s | 3.538 | 2.182 |
| 1.00 s | 3.129 | 2.115 |
| | cochlea, $|A \cdot L| = 30\pi\sqrt{2}$ | |
| 0.01 s | n/a[1] | 4.448 |
| 0.05 s | 2.917 | 3.838 |
| 0.10 s | 4.479 | 4.298 |
| 0.50 s | 4.285 | 2.118 |
| 1.00 s | 4.941 | 1.466 |

[1] no legal value was found for $f_c$

TABLE 2

| $t_{STIM}$ | $f_{MAX}$ = 10 kHz | $f_{MAX}$ = 100 kHz |
|---|---|---|
| | full-body, $|A \cdot L| = 10\pi\sqrt{2}$ | |
| 0.01 s | 30.9% | 7.23% |
| 0.05 s | 5.66% | 17.0% |
| 0.10 s | 7.23% | 18.6% |
| 0.50 s | 17.0% | 17.2% |
| 1.00 s | 18.6% | 16.6% |
| | cochlea, $|A \cdot L| = 30\pi\sqrt{2}$ | |
| 0.01 s | n/a[1] | 2.34% |
| 0.05 s | 3.32% | 4.39% |
| 0.10 s | 2.29% | 6.05% |
| 0.50 s | 2.83% | 6.35% |
| 1.00 s | 4.30% | 2.69% |

[1] no legal value was found for $f_c$

TABLE 3

| $t_{STIM}$ | $f_{MAX}$ = 10 kHz | $f_{MAX}$ = 100 kHz |
|---|---|---|
| full-body, $|A \cdot L| = 10\pi\sqrt{2}$ | | |
| 0.01 s | 15.2% | 4.88% |
| 0.05 s | 3.91% | 6.84% |
| 0.10 s | 4.88% | 7.23% |
| 0.50 s | 6.84% | 6.64% |
| 1.00 s | 7.23% | 6.84% |
| cochlea, $|A \cdot L| = 30\pi\sqrt{2}$ | | |
| 0.01 s | n/a[1] | 1.56% |
| 0.03 s | 1.17% | 2.05% |
| 0.10 s | 1.56% | 2.34% |
| 0.50 s | 1.90% | 2.44% |
| 1.00 s | 2.05% | 1.86% |

[1]no legal value was found for $f_c$ in Tables 1, 2, and 3 support the general trend of increased peak height and broadened spatial peak width with increased $t_{STIM}$ and/or $f_{MAX}$, to a point, after which the values decrease.

To understand this behavior, we must explore the relationship among $t_{STIM}$, $t_{pBEST}$, $f_c$, and $f_{MAX}$. According to (25) there is a relationship between stimulation time $t_{STIM}$, pulse width $t_p$, and velocity, through the dimension(s) of the wave-guiding structure; according to (10), $t_p$ is also related to bandwidth $f_w$. Consider $\phi=(f_{MAX}-f_c)/f_w$ as an index of "gain power." An increase in $f_{MAX}$ results in a quasi-proportional increase in $f_c$ (FIG. 9A) leading to a proportional increase in $\phi$. Similarly, the same increase in $t_p$ results in a proportional decrease in $f_w$ leading to the same proportional increase in $\phi$. Therefore, increases in $f_{MAX}$ are identical at the first order to proportional increases in $t_p$ and therefore $t_{STIM}$.

FIG. 9B illustrates the dependence of $t_{pBEST}$ on $f_{MAX}$. As shown, the value increases toward the limit of $t_{STIM}$ with increasing $f_{MAX}$. As a result, higher values of $f_{MAX}$ (or higher values of $t_{STIM}$) will eventually lead to $t_{pBEST} \geq t_{STIM}/2$. These larger values lead to additional, undesired interference near the entrance to the wave-guiding structure, an effect illustrated in FIG. 6D.

One final relation is that of gain and spatial resolution as the waveguide dimensional value A·L varies. Since A is intrinsically linked to $v_M$, the overall waveform velocities are also linked to A, such that smaller values of A lead to larger velocities. The length of the waveguide will also influence the resolution, as longer waveguides require larger velocities for a given $t_{STIM}$. Together, A·L is a dimensionless value that indexes resolution. For example, if two waveguides have equal cross-section, but one is longer, the longer waveguide will produce improved resolution and gain scores.

Figure 10:
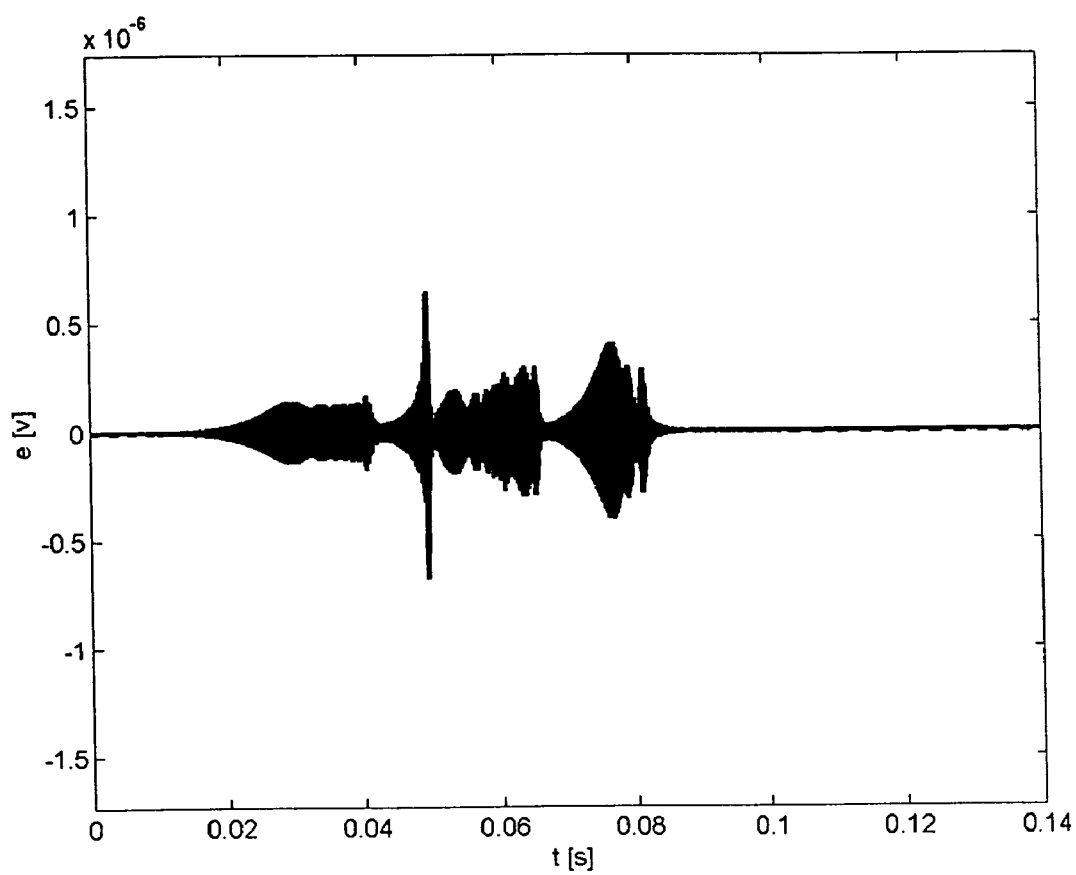
FIG. 10 shows a typical input signal to the waveguide.
Figure 11:
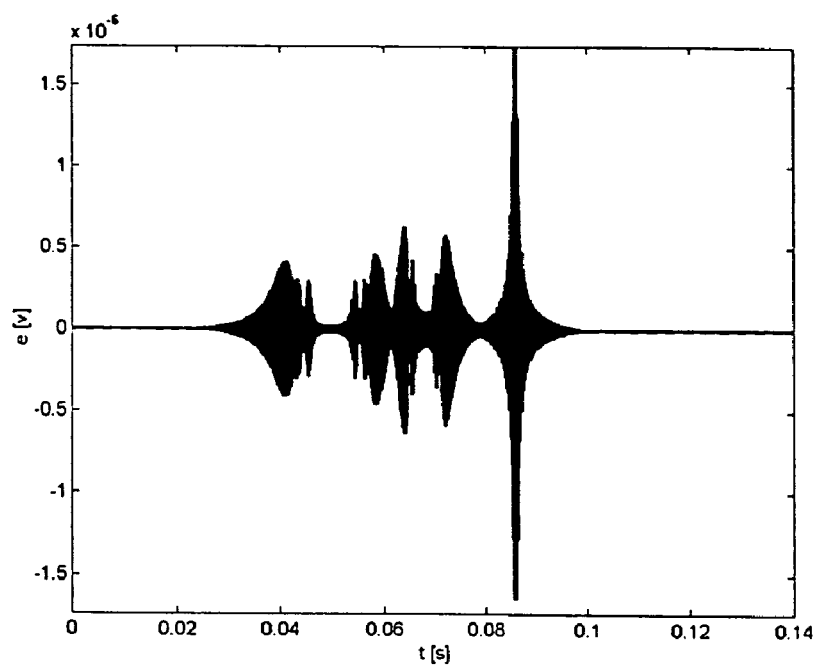
FIG. 11A shows a typical stimulation signal at a target.
FIG. 11B shows the same plot but zoomed in on the main stimulation peak.
Figure 11:
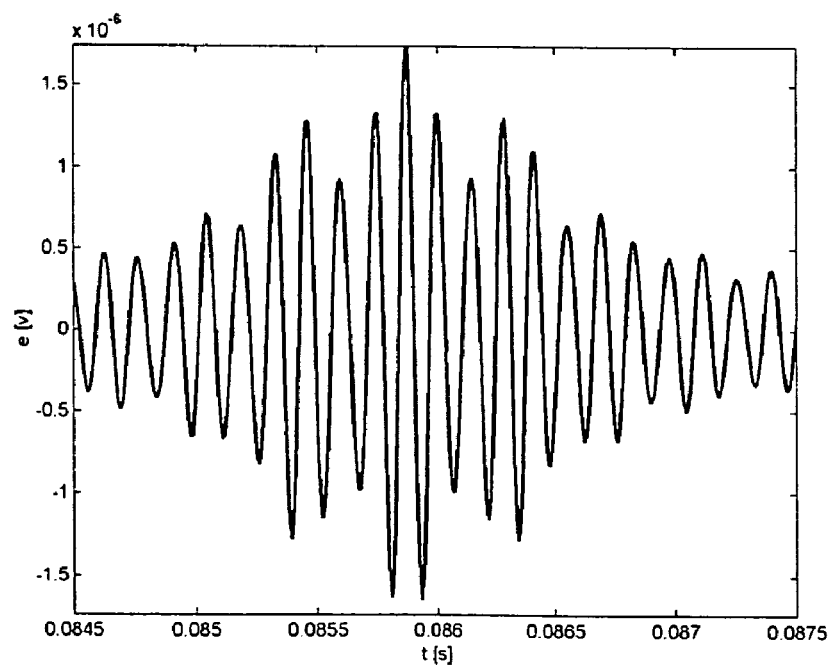

Two important benefits of this technique are (1) the ability to deliver stimulation at any location within the geometry of the wave-guiding structure and (2) control over the size of the target stimulation area. The first benefit does not require any information about the desired stimulation location(s) prior to the design, construction, and placement of the device. Instead, the appropriate stimulation waveform (equation 9) can be calculated and stored in advance, requiring only the final phase compensation to derive the input excitation waveform. In FIG. 10, the input signal was derived to create the stimulation pattern of FIG. 4. FIG. 11A shows the resulting excitation signal at the 29 mm target, and FIG. 11B shows a close-up on the stimulation peak. FIGS. 10, 11A, and 11B all plot field intensity as a function of time.

The second benefit, control over the affected target area, is determined by the specific choice of parameters $t_{STIM}$, $f_{MAX}$, and percent overlap, in conjunction with the geometry of the wave-guiding structure. There is a tradeoff between these parameters, as smaller $t_{STIM}$ or $f_{MAX}$ values decrease the sharpness of the stimulation resolution, and very high signal overlap (i.e., >95%) will also degrade spatial resolution. The cross-sectional geometry, which relates to $v_M$ by (22), also affects spatial resolution because $v_M$ is linked to the overall stimulation time by (25).

In practice, the propagation constant, $\beta$, for the specific stimulation paradigm must be measured and accounted for before stimulation. This will likely affect the interaction between the material composing the core of the wave-guiding structure and the target tissue. Additionally, the specific energy requirements must be examined for each scenario.

A low propagation velocity ($v_M$) is desired in the waveguide. According to (22), $v_M = f_c/A$, where $A = \pi\sqrt{2}$ mm$^{-1}$ for the small-scale cochlear waveguide and $A = 4\pi\sqrt{2}$ m$^{-1}$ for the large-scale full body waveguide. Due to the tradeoff between electrical and thermal excitation discussed in the above-referenced book by Geddes and Baker, it is necessary to use low frequencies (e.g., below 100 kHz). Therefore $$f_{MAX} \leq 100 \text{ kHz} \qquad (34)$$

$$\longrightarrow f_c < 100 \text{ kHz}$$

$$\longrightarrow v_M < \frac{10^5}{|A|} \text{m/s},$$

where the maximum velocity within free space is approximately $3 \times 10^8$ m/s.

The theoretical maximum velocity of electromagnetic waves within a given medium is related to the permittivity ($\in$) and permeability ($\mu$) of that medium:

$$v_M = \frac{1}{\sqrt{\mu\epsilon}}. \qquad (35)$$

It is therefore possible to attain this velocity through materials exhibiting large values of relative permittivity and permeability. Reference may be had to the above-referenced Ramo et al. book as well as to the following: L. D. Landau, E. M. Lifshitz, and L. P. Pitaevskii, *Electrodynamics of Continuous Media, vol. 8 of Course of Theoretical Physics*, Butterworth-Heinemann, Oxford, second edition, 1999, translated from the Russian by J. B. Sykes, J. S. Bell and M. J. Kearsley; and Nora E. Hill, Worth E. Vaughan, A. H. Price, and Mansel Davies, *Dielectric Properties and Molecular Behaviour*, The Van Nostrand Series in Physical Chemistry, Van Nostrand Reinhold Company, New York, 1969. Some such materials have very high values, especially within the specified frequency range. See, for example, S. S. Bellad, S. C. Watawe, and B. K. Chougle, "Some AC electrical properties of Li—Mg ferrites," *Materials Research Bulletin*, Vol. 34, No. 7, pp. 1099-1106, 1999.

There are other possible ways to attain this substantial slowing including the use of acoustic waves in conjunction with piezo-electric materials (see, e.g., B. A. Auld, *Acoustic Fields and Waves in Solids*, Vol. One and Two, Robert E. Krieger Publishing Company, Malabar, Fla., second edition, 1990), "slow-wave" structures (see Ramo et al., supra, and R. E. Collin, *Field Theory of Guided Waves*, McGraw-Hill Book Company, Inc., New York, 1960), and ultra-slowed group velocities brought about by electromagnetic induced transparency (EIT; see Michael M. Kash et al., "Ultraslow group velocity and enhanced nonlinear optical effects in a coherently driven hot atomic gas," *Physical Review Letters*, Vol. 82, No. 26, pp. 5229-5232, June 1999; and Chien Liu, Zachary Dutton, Cyrus H. Behroozi, and Lene Vestergaard Hau, "Observation of coherent optical information storage in an atomic medium using halted light pulses," *Nature, Vol.* 409, pp. 490-493, January 2001.)

Finally, the necessary velocities are always attainable by approaching $f_c$. The goal is therefore to provide a cutoff within the allowable range. Certain waveguides (e.g., surface waveguides discussed in the Ramo et al. and Collin books cited above) exhibit cutoff frequencies as low as 0 Hz. All of the above-cited references are hereby incorporated by reference in their entireties.

Since the target is influenced directly by the phase delay for the constituent pulses comprising the entire excitation signal, the choice of the target is made before the excitation signal is presented to the waveguide. This may be done with control technology at the front end of the stimulating device. A processor may be employed which decides where the stimulus must occur and then constructs the excitation signal for the guide. Processor circuitry and techniques for determining where to stimulate are disclosed in the following references, which are hereby incorporated by reference into this patent application: 1) Philipos C. Loizou, "Signal-Processing Techniques for Cochlear Implants," *IEEE Engineering in Medicine and Biology*, May/June 1999, pp. 34-46; and 2) U.S. Pat. No. 4,495,384 to Scott et al. In fact, most pre-processing can be done outside of the body. Once the excitation signal is constructed, it can be transmitted to the implanted device, which need only consist of a receiver/decoder, amplifier, and the actual waveguide. This creates a large degree of flexibility for developing control technologies, since progressing work on the quality and type of stimulation signal can still readily utilize the existing implant.

In summary, the invention provides a new method for stimulation that can be used in the place of conventional electrode stimulation. The benefits of this method include (1) the ability to deliver stimulation at any location within the geometry of the wave-guiding structure and (2) control over the size of the target stimulation area. These properties depend upon the stimulation time, allowable frequency range, tissue geometry, and a well-defined knowledge of the tissue properties. We have demonstrated that the method is scalable, and can therefore be used for both small-scale, implantable devices and large-scale, external devices.

Since the method is scalable, a large-scale test device using much higher frequencies, e.g., microwave frequencies, can be tested for field distribution. One such device contemplated by the present invention is a waveguide designed to externally stimulate invertebrate excitable tissue, e.g., a squid axon. The waveguide may be a cylindrical waveguide constructed of high-conductance metal with a radius two to ten times that of the squid axon to be stimulated, and with a length approximately twice the axon length. The waveguide entrance is constructed to accommodate radiant electromagnetic input, i.e., from an antenna, as well as suspension of the squid axon with a suitable support medium. The far end of the waveguide is sealed with the same high-conductance metal to create reflections. For a given target location within the tissue, the appropriate input signal may be derived computationally and output digitally from a computer, passed through a digital-to-analog converter and then through a linear amplifier having an output connected to the antenna.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

We claim:

1. A method of stimulating electrically excitable living tissue, comprising:
    positioning an electromagnetic waveguide adjacent to a target tissue along a length of said tissue having a plurality of electrically excitable target locations; and
    delivering an excitation signal to said waveguide designed to produce a plurality of electric field pulses with frequencies below approximately 100 kHz within said waveguide so as to create constructive interference at a selected target location therein corresponding to one of said target locations along the length of said tissue, thereby electrically stimulating said target tissue at a selected target location along the length thereof;
    wherein said frequencies are above the cutoff frequency of said waveguide and below 100 kHz.

2. The method of claim 1, wherein said plurality of electric field pulses includes pulses with different propagation velocities produced within said waveguide at different times.

3. The method of claim 1, wherein said plurality of electric field pulses includes pulses with different propagation velocities and corresponding delays selected so as to coalesce at said desired location with minimal overlap of pulses away from said desired location.

4. The method of claim 1, wherein said positioning comprises implanting said waveguide within an animal body.

5. A method of stimulating electrically excitable living tissue, comprising:
    positioning an electromagnetic waveguide adjacent to a target tissue along a length of said tissue having a plurality of electrically excitable target locations; and
    delivering an excitation signal to said waveguide designed to produce a plurality of electric field pulses with frequencies below approximately 100 kHz within said waveguide so as to create constructive interference at a selected target location therein corresponding to one of said target locations along the length of said tissue, thereby electrically stimulating said target tissue at a selected target location along the length thereof;
    wherein said plurality of electric field pulses includes forward traveling pulses and reflected pulses within said waveguide,
    wherein constructive interference is created between said reflected pulses and forward traveling pulses within said waveguide, and
    wherein said positioning comprises implanting said waveguide within an animal body, with a reflective boundary at the far end of said waveguide positioned beyond at least one of said target locations along the length of said tissue.

6. A method of stimulating electrically excitable living tissue, comprising:
    positioning an electromagnetic waveguide adjacent to a target tissue along a length of said tissue having a plurality of electrically excitable target locations; and
    delivering an excitation signal to said waveguide designed to produce a plurality of electric field pulses with frequencies below approximately 100 kHz within said waveguide so as to create constructive interference at a selected target location therein corresponding to one of said target locations along the length of said tissue, thereby electrically stimulating said target tissue at a selected target location along the length thereof;

wherein said positioning comprises implanting said waveguide within a cochlea of an animal body, with said waveguide having two parts extending through respective spiral canals of the cochlea.

7. The method of claim 6, wherein said frequencies are above the cutoff frequency of said waveguide and below 100 kHz.

8. The method of claim 6, wherein said positioning comprises implanting said waveguide within an animal body, with a reflective boundary at the far end of said waveguide positioned beyond at least one of said target locations along the length of said tissue.

* * * * *